United States Patent
Yamamoto et al.

[11] Patent Number: 6,111,258
[45] Date of Patent: Aug. 29, 2000

[54] METHOD FOR WORKING IN A SPECIMEN AND A STAGE FOR THE METHOD

[75] Inventors: Takekazu Yamamoto, Tokyo; Masayoshi Momiyama, Ichikawa; Naoto Kagiyama; Naritoshi Kanai, both of Tokyo, all of Japan

[73] Assignee: Aisin Seiki Kabushiki Kaisha, Kariya, Japan

[21] Appl. No.: 09/238,154

[22] Filed: Jan. 28, 1999

[30] Foreign Application Priority Data

Jan. 30, 1998 [JP] Japan ................................. 10-019055
May 18, 1998 [JP] Japan ................................. 10-135179

[51] Int. Cl.[7] .............................. G01J 1/88; G01N 21/64
[52] U.S. Cl. ..................................... 250/458.1; 250/461.2
[58] Field of Search ............................ 250/458.1, 461.1, 250/461.2; 204/461, 612; 382/128, 129

[56] References Cited

U.S. PATENT DOCUMENTS

| 4,877,965 | 10/1989 | Dandliker et al. | 250/458.1 |
| 5,091,652 | 2/1992 | Mathies et al. | 250/458.1 |
| 5,242,567 | 9/1993 | Fujimiya et al. | 204/299 |

FOREIGN PATENT DOCUMENTS

| 6-308118 | 11/1994 | Japan . |
| 7-318782 | 12/1995 | Japan . |
| 8-234110 | 9/1996 | Japan . |

*Primary Examiner*—Frank G. Font
*Assistant Examiner*—Zandra Smith
*Attorney, Agent, or Firm*—Oblon, Spivak, McClelland, Maier & Neustadt, P.C.

[57] ABSTRACT

A method for working in a specimen includes the steps of (a) putting the specimen on a stage; (b) irradiating radiation to the specimen for excitation; (c) recording detected characteristics of the excited specimen by the radiation; (d) displaying the recorded characteristics on the stage; (e) storing the recorded characteristics of the excited specimen; (f) maintaining display of the stored characteristics on the stage; and (g) working on the specimen on the stage over the displayed characteristics. An operator may easily access to the specimen with a scalpel or a knife since the detected characteristics are displayed on the stage after the detection of the characteristics. Even if the detection requires harmful radiation such as ultraviolet light, the operator may work in the specimen after turning off such harmful radiation. Therefore, the operator does not have to wear any protection against the harmful radiation so as to work in the specimen more easily and efficiently. Further, according to the present invention, a very delicate specimen, such as deoxyribonucleic acid, may be analyzed with less deterioration of the specimen since the excitation radiation is not necessary during the work in the specimen. In fact, a momentary excitation radiation may be sufficient to display the necessary characteristics on the stage.

12 Claims, 6 Drawing Sheets

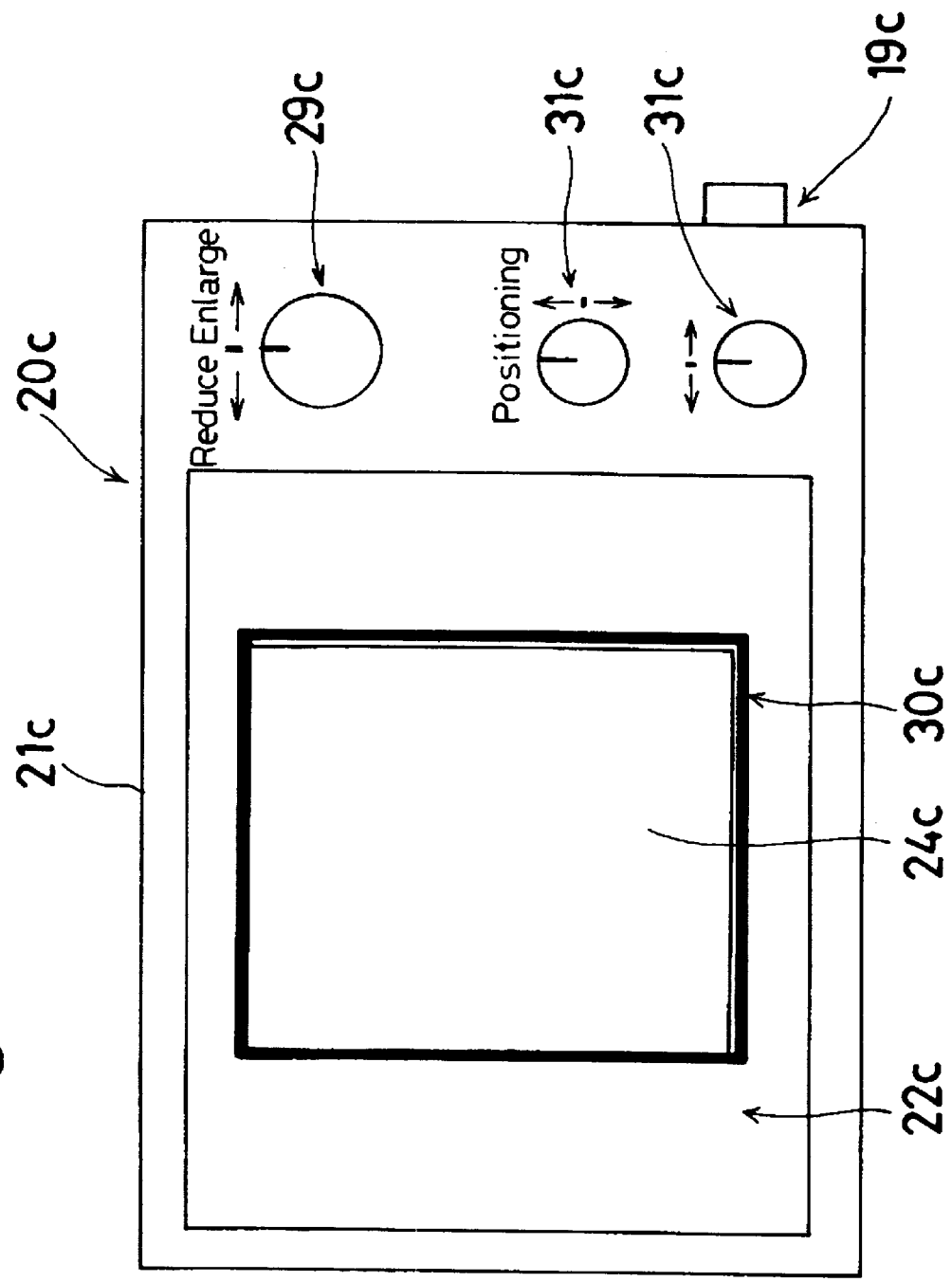

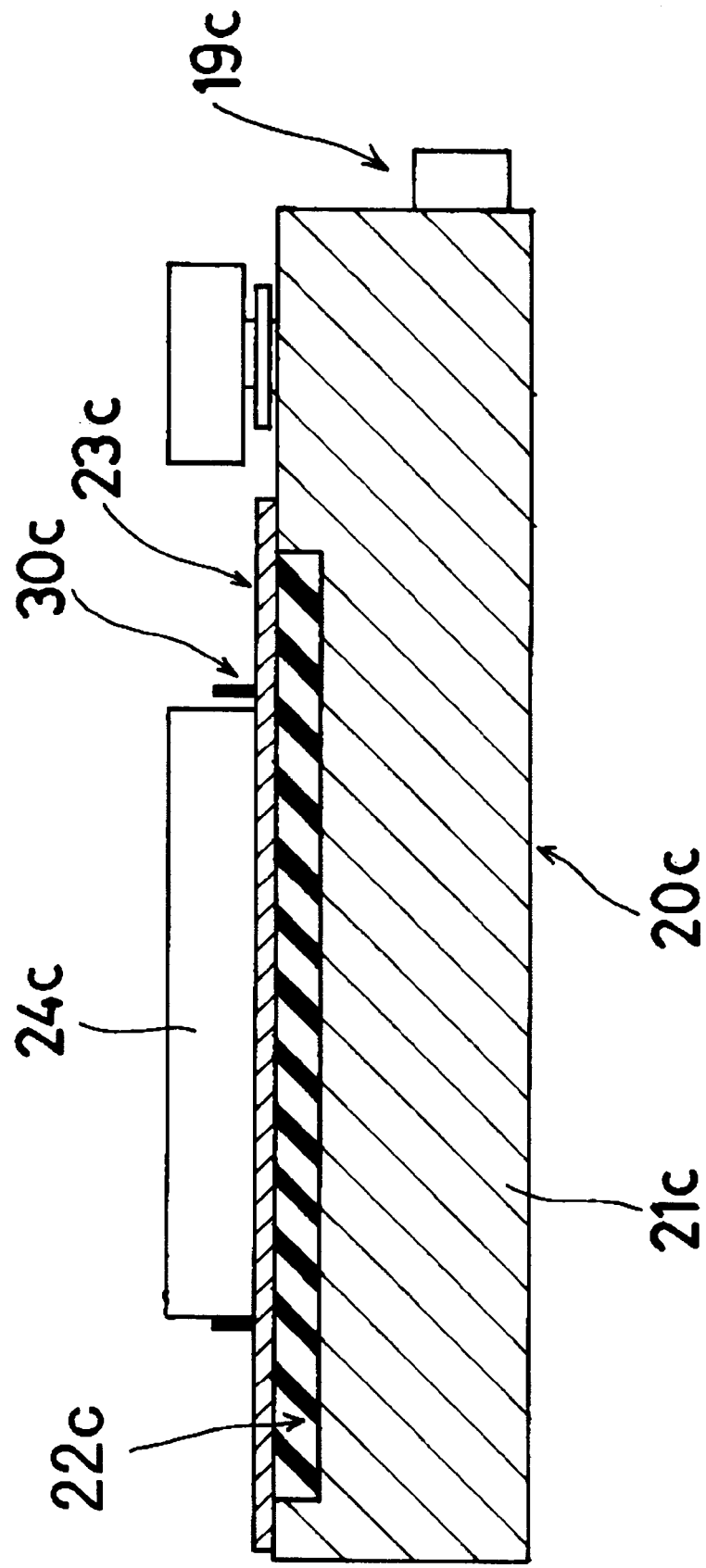

METHOD FOR WORKING IN A SPECIMEN AND A STAGE FOR THE METHOD

BACKGROUND OF THE INVENTION

1. Field of the Invention

This application claims priority under 35 U.S.C. §§ 119 and/or 365 to "Method for Working in a Specimen and a Stage for the Method," Application No. H10-019055 filed in JAPAN on Jan. 30, 1998 and Method for Working in a Specimen and a Stage for the Method," Application No. H10-135179 filed in JAPAN on May 18, 1998, the entire content of both of which is herein incorporated by reference.

This invention relates to analyzing method of a specimen using a fluorescence analyzer.

2. Description of the Related Art

In order to observe a gel specimen treated by electrophoresis, the specimen is exposed to excitation light so that the specimen generates fluorescence light to be detected by a photo detector. Two types of illuminators are known in the art to irradiate the specimen with the excitation light. One is the transparent illuminator and the other is the reflective illuminator. In the transparent illuminator, the excitation light penetrates the specimen toward the photo detector. In the reflective illuminator, the excitation light reflects on the specimen toward the photo detector. The reflective illuminator is more reliable than the transparent illuminator due to less amount of the excitation light that directly reaches to the photo detector. Therefore, the reflective illuminator is preferred for various fluorescence analyzers such as the spectroscopic fluorescent photometer and the fluorescent microscope.

The publication "ILLUSTRATED BIOLOGICAL EXPERIMENTS VOL.2" published in Japan by SHUJUN-SHA Co., Ltd. on Sep. 25, 1995 discloses a working method to extract deoxyribonucleic acid from gel. In Chapter 3, paragraph 4 of this publication, a gel specimen is put on the transparent illuminator to be exposed by the excitation light. The essential deoxyribonucleic acid band may be cut and extracted with a scalpel or a knife under see-through observation of an electrophoresis pattern over the transparent illuminator.

However, due to the transparent illuminator the operator has to wear a face shield and gloves to be protected from the harmful excitation radiation such as ultraviolet light. Further, a dark room is required for the work. Accordingly, the work of accessing the specimen may become inefficient.

On the other hand, the reflective illuminator may not be suitable for the work since the scalpel or the knife may not be used over the gel specimen. Such tools may block off the excitation light so that the electrophoresis pattern is hardly observed with the reflective illuminator.

SUMMARY OF THE INVENTION

Accordingly, one of the objects of the present invention is to solve the above conventional drawbacks.

Another object of the present invention is to analyze a specimen more efficiently.

Yet another object of the present invention is to work in a specimen more efficiently.

Yet a further object of the present invention is to access to a specimen more easily.

In order to achieve the above and other features, the present invention comprises steps of (a) putting the specimen on a stage; (b) irradiating radiation to the specimen for excitation; (c) detecting and recording characteristics of the specimen excited by the radiation; (d) displaying the recorded characteristics on the stage; (e) storing the recorded characteristics of the excited specimen; (f) maintaining display of the stored characteristics on the stage; and (g) working in the specimen on the stage over the displayed characteristics.

The operator may easily access the specimen with the scalpel or the knife since the recorded characteristics are kept displayed on the stage after the detection of the characteristics. If the detection requires harmful radiation such as ultraviolet light, the operator may work on the specimen after turning off such harmful radiation. Therefore, the operator does not have to wear protection against the harmful radiation, and may work on the specimen more easily and efficiently.

Further, according to the present invention, a very delicate specimen, such as deoxyribonucleic acid, may be analyzed with less deterioration of the specimen since the excitation radiation is not necessary during the work on the specimen. In fact, a momentary excitation radiation may be sufficient to display the necessary characteristics on the stage.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 6 shows a plan view of a stage according to a fourth embodiment of the present invention; and FIG. 7 shows a cross sectional view of a stage according to the fourth embodiment of the present invention.

DETAILED DESCRIPTION OF THE PREFERRED EMBODIMENTS

Figure 1:
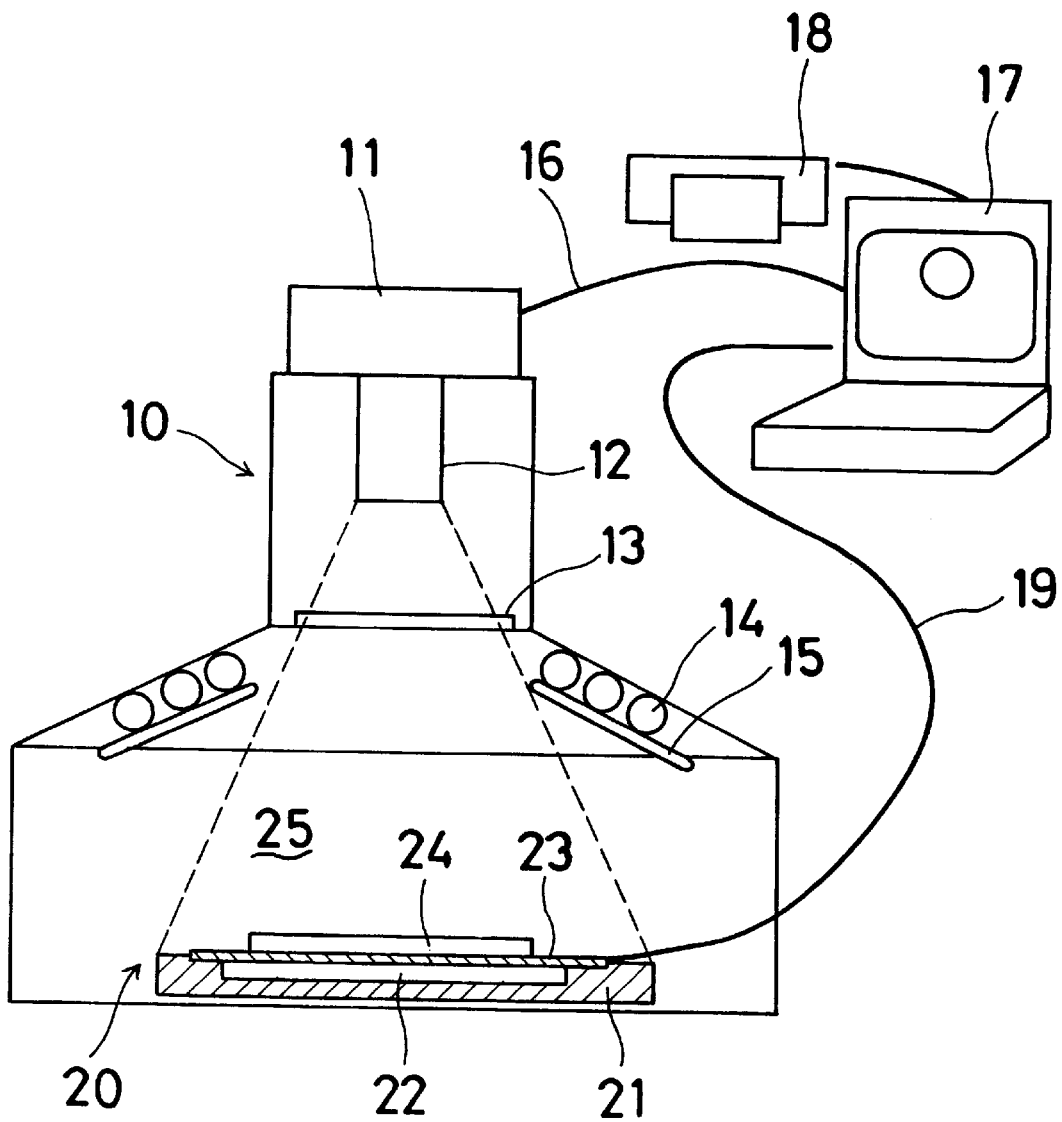
FIG. 1 shows a schematic view of a stage according to a first embodiment of the present invention.

FIG. 1 shows a schematic view of a stage according to the first embodiment of the present invention.

A stage 20 is installed in a reflective illuminator 10. The stage 20 comprises a base 21, a liquid crystal display 22 and a cover glass 23. The liquid crystal display 22 and the cover glass 23 are fixed to the base 21. The liquid crystal display 22 is overlaid with the cover glass 23. A gel specimen 24 is put on the cover glass 23.

A reflective illuminator 10 comprises an ultraviolet lamp 14 and a filter 15. The ultraviolet lamp 14 emits excitation light at 312 nanometers so as to irradiate an irradiation area 25 through the filter 15. The filter 15 selectively passes ultraviolet light at 312 nanometers. The stage 20 is disposed in the irradiation area 25. The characteristics of the irradiation area 25 are detected and recorded, e.g., they are photographed by a camera 11 through a filter 13 and a zoom lens 12, although the camera may be replaced by any other recording device which is capable of detecting and recording a characteristic of the irradiated area. "Recording" here means only that the characteristic is captured with sufficient permanence that it can later be displayed on the stage. The camera 11 may employ a charge-coupled device.

The photographed image is received by a computer 17 through a wire 16. The computer 17 stores the image data in a storage device and displays the photographed image via a built-in monitor. The photographed image is further transmitted from the computer 17 to the liquid crystal display 22 of the stage 20 through a wire 19. The liquid crystal display 22 displays the life-size image at the exact location of the irradiation area 25 so that the photographed image of the gel specimen 25 agrees with the gel specimen 24.

When the ultraviolet lamp 14 is lit, the gel specimen 24 is irradiated by the ultraviolet light at 312 nanometers on the stage 20. Illuminator contained in the gel specimen 24 illuminates in response to the irradiated ultraviolet light. The camera 11 photographs the image of the illuminated gel specimen 24. The computer 17 stores and displays the photographed image of the illuminated gel specimen 24. The operator may confirm the photographed image at the computer 17. After the photographed image is captured, the ultraviolet lamp 14 is turned off and the photographed image is displayed on the liquid crystal display 22. The operator may cut the essential parts of the gel specimen 24 with the scalpel or the knife under see-through observation of the photographed image over the liquid crystal display 22.

In order to perfectly align the photographed image with the actual gel specimen 24 over the liquid crystal display 22, the position and the magnification of the photographed image have to be adjusted in accordance with relative positions of the camera 11 and the stage 20. For these adjustments, one or more marks (not shown) may be printed on the stage 20 or otherwise associated with predetermined positions of the stage. For example, the computer 17 may be programmed so as to align the photographed image with the actual gel specimen 24 over the liquid crystal display 22 when the operator adjusts the position and magnification of the photographed image so that the marks are fully displayed in the built-in monitor of the computer 17 at the maximum size. In this case, the marks provide a fixed reference for the alignment of the image with the actual gel specimen.

With the marks printed on the stage 20, the gel specimen 24 may be photographed separately from the stage 20. To make this possible, a holder (not shown) may be used to hold the gel specimen 24 when the gel specimen 24 is photographed in the reflective illuminator 10. After the photograph, the operator may precisely position the holder on the stage using the marks printed on the stage 20 in order to easily put the gel specimen 24 on the stage 20 at the right position.

It is within the scope of the invention for the photographed or otherwise recorded image to be transferred to the stage and aligned manually and without the aid of the computer.

Further, a preferred magnification of the zoom lens 12 may be preset for easy operation. It is within the skill of one skilled in the art to preset the preferred magnification electronically in the computer 17 using a built-in potentiometer (not shown) of the zoom lens 12. It is also within the skill of one skilled in the art to record the preferred magnification by a sticker (not shown) that is adhered to a dial gauge (not shown) of the zoom lens 12.

The cover glass 23 protects the liquid crystal display 22 against scratches made by the scalpel or the knife.

Figure 2:
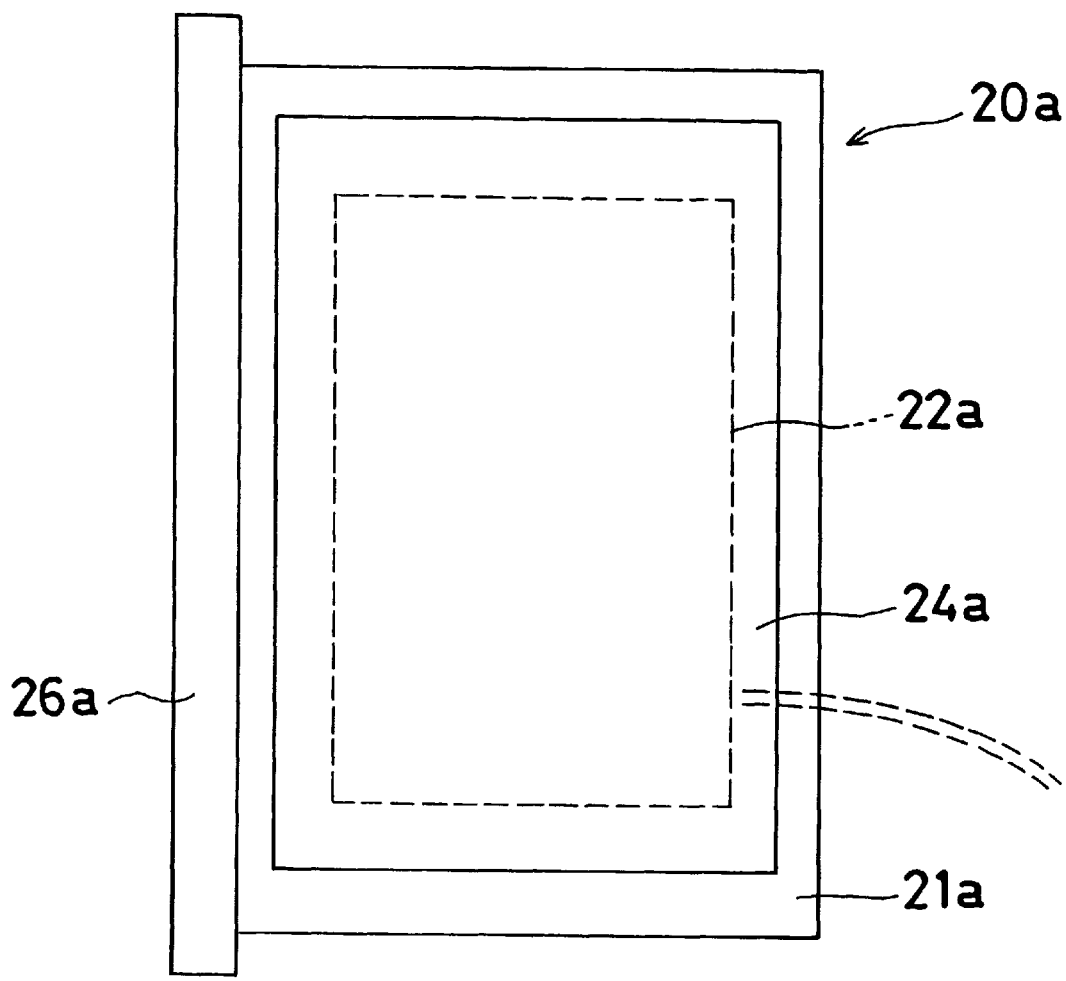
FIG. 2 shows a plan view of a stage according to a second embodiment of the present invention.
Figure 3:
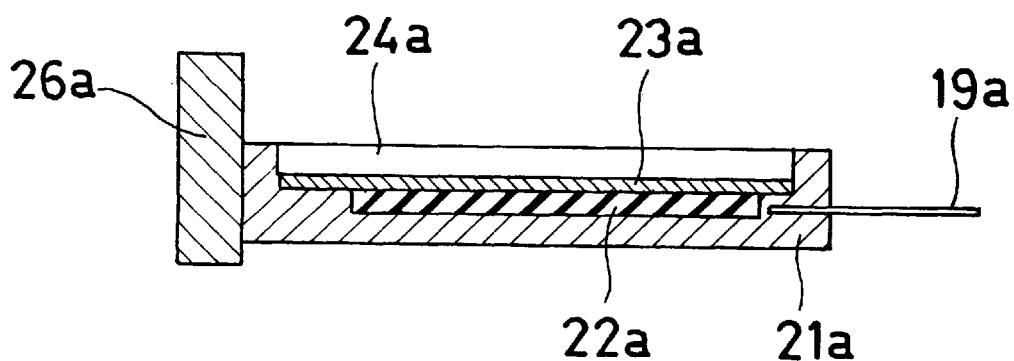
FIG. 3 shows a cross sectional view of a stage according to the second embodiment of the present invention.

The stage 20 may be removed from the reflective illuminator 10. FIGS. 2 and 3 show a removable stage 20*a* according to the second embodiment of the present invention.

The removable stage 20*a* comprises a liquid crystal display 22*a* mounted on a base 21*a*. The liquid crystal display 22*a* is overlaid by a cover glass 23*a* for protection. The cover glass 23*a* is clear and transparent. A gel specimen 24*a* is put on the cover glass 23*a*. A handle 26*a* is fixed to a side of the base 21*a*. The removable stage 20*a* may slide in right and left directions in FIGS. 2 and 3 with respect to the reflective illuminator 10 so as to insert/remove the removable stage 20*a* into/from the reflective illuminator 10. The operator may cut the essential parts of the gel specimen 24*a* with the scalpel or the knife under see-through observation of the photographed image over the liquid crystal display 22*a*. In the second embodiment, the operator may access to the gel specimen 24*a* outside the reflective illuminator 10.

Figure 4:
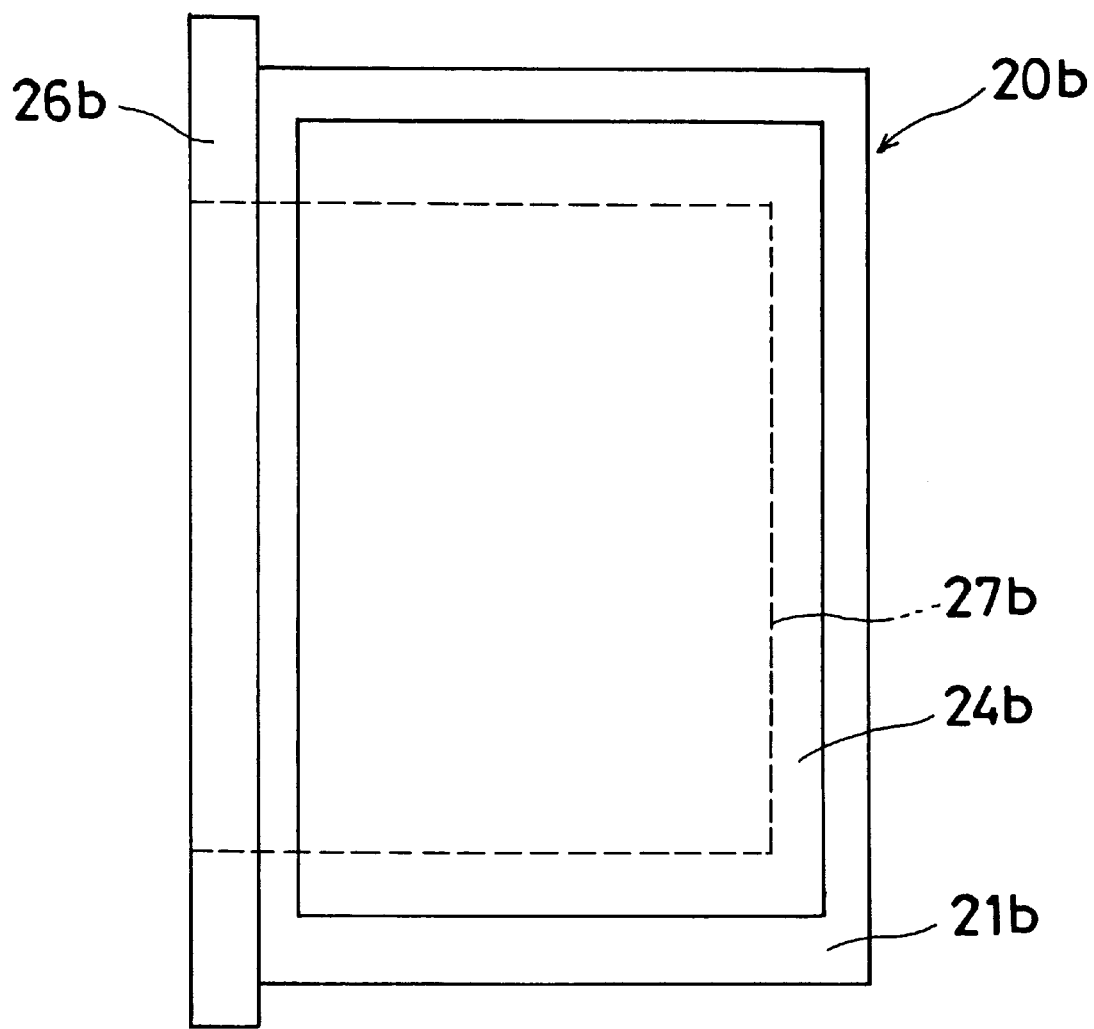
FIG. 4 shows a plan view of a stage according to a third embodiment of the present invention.
Figure 5:
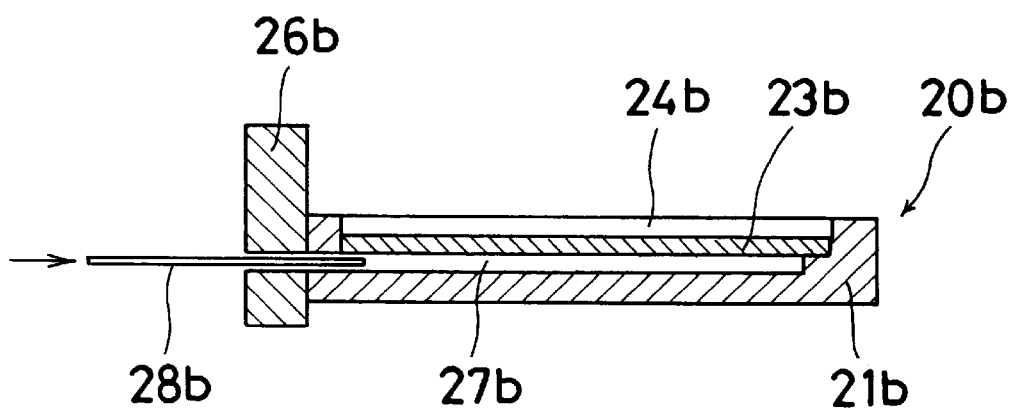
FIG. 5 shows a cross sectional view of a stage according to a third embodiment of the present invention.

FIGS. 4 and 5 show a removable stage 20*b* according to the third embodiment of the present invention.

The removable stage 20*b* has a space 27*b* provided in the base 21*b*. The space 27*b* is overlaid by a cover glass 23*b* for protection. The glass 23*b* is clear and transparent. A gel specimen 24*b* is put on the cover glass 23*b*. A handle 26*b* is fixed to a side of the base 21*b*.

The removable stage 20*b* may slide in right and left directions in FIGS. 4 and 5 with respect to the reflective illuminator 10 so as to insert/remove the removable stage 20*b* into/from the reflection illuminator 10. Instead of a liquid crystal display, a printout 28*b* is inserted into the space 27*b*. The printout 28*b* is printed by a printer 18 shown in FIG. 1. The computer 17 transmits the photographed image of the illuminated gel specimen 24*b* to the printer 18. The printout 28*b* has the electrophoresis pattern of the illuminated gel specimen 24*b* that is exactly the same size of the actual gel specimen 24*b*. The operator may cut the essential parts of the gel specimen 24*b* with the scalpel or the knife under see-through observation of the electrophoresis pattern over the printout 28*b*. In the third embodiment, no liquid crystal display is required so as to be less expensive. Instead of the printout 28*b*, a life-size photograph taken by the camera 11 may also be used in the space 27*b*.

It is within the skill of one skilled in the art to project the photographed image stored in the computer 17 onto the surface of the stage 20 without departing from the spirit of the present invention.

FIGS. 6 and 7 show a removable stage 20*c* according to the fourth embodiment of the present invention.

The removable stage 20*c* comprises a liquid crystal display 22*c* mounted on a base 21*c*. The liquid crystal display 22*c* is overlaid by a cover glass 23*c* for protection. The cover glass 23*c* is clear and transparent. A gel specimen 24*c* is put on the cover glass 23*c*. An adjusting knob 29*c* is provided on the removable stage 20*c* in order to adjust the magnification of the photographed image displayed in the liquid crystal display 22*c*. The operator may adjust the size of the photographed image in accordance with the actual size of the gel specimen 24*c*. Further, two additional knobs 31*c* are provided on the removable stage 20*c* in order to adjust vertical and horizontal positions of the photographed image displayed in the liquid crystal display 22*c*. The operator may adjust the position of the photographed image to perfectly agree with the actual position of the gel specimen 24*c*. The adjusting knobs 29*c*, 31*c* and the liquid crystal display 22*c* are electrically connected to the computer 17 through the connector 19*c* and the wire 19. Further, a specimen holder 30*c* is provided on the cover glass 23*c*. The operator may cut the essential parts of the gel specimen 24*c* with the scalpel or the knife under see-through observation of the photographed image over the liquid crystal display 22c. Due to the specimen holder 30c, the gel specimen 24c is secured on the stage 20c so that the gel specimen 24c is not off from the original position. In the fourth embodiment, the operator may access the gel specimen 24c outside the reflective illuminator 10.

Further, in case the stage 20c cannot be installed in the reflective illuminator 10, the gel specimen 24c alone may be photographed separately from the stage 20c. After making the photograph, the operator may put the gel specimen 24c on the stage 20c where the liquid crystal display 22c displays the photographed image. In this way, the operator may also access the gel specimen 24c outside the reflective illuminator 10.

It may be within the skill of one skilled in the art to use other image capturing devices, image processing devices and image displays instead of the camera 11, computer 17 and liquid crystal displays 22, 21a, 22c.

In the embodiments of the present invention, the gel specimens 24, 24a, 24b and 24c are disposed in the reflective illuminator 10 after the gel specimens 24, 24a, 24b and 24c are put on the stages 20, 20a, 20b and 20c. Then the characteristics of the gel specimens 24, 24a, 24b and 24c are photographed under irradiation of the ultraviolet lamp 14 so that the photographed images of the gel specimens 24, 24a, 24b and 24c are displayed on the stages 20, 20a, 20b and 20c at life-sizes. Due to the life-size display on the stages 20, 20a, 20b and 20c, the operator may work on the gel specimens 24, 24a, 24b and 24c without harmful ultraviolet light. Therefore, the operator may access to the gel specimens 24, 24a, 24b and 24c very efficiently and safely.

Further, in the embodiments of the present invention, the liquid crystal displays 22, 22a, 22c and the printout 28b display the photographed image in the stages 20, 20a, 20b and 20c under the gel specimens 24, 24a, 24b and 24c.

Therefore, the stages 20, 20a, 20b and 20c may be utilized as specimen trays to hold the gel specimens 24, 24a, 24b and 24c both inside and outside of the reflect-illuminator 10. Further, the operator may work on the gel specimens 24, 24a, 24b and 24c on the stages 20, 20a, 20b and 20c since the stages 20, 20a, 20b and 20c are capable of displaying the photographed images without any concern for the ultraviolet light for excitation.

Furthermore, the reflective-illuminator 10 may be used for cutting the essential parts of the gel specimens 24, 24a, 24b and 24c with the scalpel or the knife under see-through observation of the illuminated gel specimens 24, 24a, 24b and 24c. The operator may work on the gel specimens 24, 24a, 24b and 24c easily since the photographic sensitivity and the resolution of the reflective-illuminator 10 is better than the translucent illuminator. Further, the operator may work on fewer amounts of the gel specimens 24, 24a and 24b.

In the second, third and fourth embodiments of the present invention, removable stages 20a, 20b and 20c are employed. Therefore, the operator may work on the gel specimens 24a, 24b and 24c without any restriction due to the reflect-illuminator 10. Therefore, the operator may work on the gel specimens 24a, 24b and 24c even more easily and efficiently.

In the first, the second and the fourth embodiments of the present invention, the liquid crystal displays 22, 22a and 22c are employed for displaying the photographed images. Therefore, the stages 20, 20a and 20c may be very compact and handy since the liquid crystal displays 22, 22a and 22c are very thin and flat. Further, the operator may adjust the position and the magnification of the photographed images accurately and easily. Therefore, the operator may work on the gel specimens 24, 24a and 24c more precisely.

In the third embodiment of the present invention, a printout 28b is inserted in the space 27b. The removable stage 20b may be inexpensive since the expensive liquid crystal display is not necessary.

In the embodiments of the present invention, the operator may work on a very delicate specimen, such as deoxyribonucleic acid, with less deterioration of the specimen since the ultraviolet light for excitation is not necessary during the work on the delicate specimen. In fact, a momentary excitation radiation may be sufficient to display the photographed images on the stages 20, 20a, 20b and 20c. Therefore, the operator may work on such a delicate specimen with less deterioration.

Obviously, numerous modifications and variations of the present invention are possible in light of the above teachings. It is therefore to be understood that within the scope of the appended claims, the invention may be practiced otherwise than as specifically described herein.

What is claimed is:

1. A method for working on a specimen, comprising steps of:

putting the specimen on a stage;

exciting the specimen by irradiating the specimen with radiation;

recording at least one characteristic of the excited specimen;

displaying the at least one recorded characteristic on the stage; and working on the specimen on the stage over the displayed characteristic.

2. The method of claim 1, further comprising the step of aligning the recorded characteristic on the stage using a mark whose position on the stage is predetermined.

3. The method of claim 1, further comprising the step of:

storing the recorded characteristics of the excited specimen; and maintaining display of the stored characteristics on the stage.

4. The method of claim 1, wherein the displaying step displays the detected characteristic on the stage in full-size.

5. An apparatus for working on a specimen, comprising:

holding means for holding the specimen;

irradiating means for exciting the specimen by irradiating the specimen with radiation;

recording means for recording at least one characteristic of the excited specimen; and displaying means for displaying the recorded characteristics on the holding means.

6. The apparatus of claim 5, further comprising:

measuring means for measuring a standard position and magnification of the specimen;

adjusting means for adjusting the standard position and magnification of the specimen.

7. The apparatus of claim 5, further comprising:

storing means for storing the recorded characteristic of the excited specimen;

maintaining means for maintaining the display of the displaying means by using the stored characteristic of the excited specimen.

8. The apparatus of claim 5, wherein the displaying means displays the detected characteristic on the holding means in full-size.

9. An apparatus for working on a specimen, comprising:

a holding device for holding the specimen;

an irradiating device positioned for exciting the specimen by irradiating the specimen with radiation;

a recording device positioned for detecting and recording at least one characteristic of the excited specimen; and a display device for displaying the recorded characteristics on the holding device.

10. The apparatus of claim 9, further comprising:

a measuring device for measuring a standard position and magnification of the specimen;

an adjusting element for adjusting the standard position and magnification of the specimen.

11. The apparatus of claim 9, further comprising:

a storing device connected to the recording device for storing the recorded characteristic of the excited specimen;

a maintaining device for maintaining the display of the display device by using the stored characteristic of the excited specimen.

12. The apparatus of claim 9, wherein the display device displays the detected characteristic on the holding device in full-size.

* * * * *